(12) United States Patent
Khanna et al.

(10) Patent No.: US 8,182,986 B1
(45) Date of Patent: May 22, 2012

(54) ASSAYS FOR NUCLEIC ACID MODIFYING ENZYMES

(75) Inventors: Pyare Khanna, Fremont, CA (US); Shu-Ling Cheng, Fremont, CA (US)

(73) Assignee: Discoverx, Fremont, CA (US)

( * ) Notice: Subject to any disclaimer, the term of this patent is extended or adjusted under 35 U.S.C. 154(b) by 0 days.

(21) Appl. No.: 10/194,619

(22) Filed: Jul. 12, 2002

Related U.S. Application Data (60) Provisional application No. 60/305,047, filed on Jul. 12, 2001.

(51) Int. Cl.
*C12Q 1/68* (2006.01)
*C12Q 1/34* (2006.01)

(52) U.S. Cl. ............... 435/6; 435/7.6; 435/18; 435/69.2

(58) Field of Classification Search ................ 435/6, 18, 435/15, 7.9, 7.91, 7.4
See application file for complete search history.

(56) References Cited

U.S. PATENT DOCUMENTS

| | | | | |
|---|---|---|---|---|
| 5,200,337 | A | * | 4/1993 | Polisson et al. ............... 435/199 |
| 5,416,003 | A | * | 5/1995 | Lawrence et al. ............... 435/18 |
| 5,763,196 | A | * | 6/1998 | Powell et al. ................... 435/7.6 |
| 5,795,718 | A | * | 8/1998 | Eisenbeis ......................... 435/6 |
| 5,958,692 | A | * | 9/1999 | Cotton et al. .................... 435/6 |

OTHER PUBLICATIONS

Altrogge et al., Analytical Biochemistry vol. 277, pp. 33-45, 2000.*

* cited by examiner

*Primary Examiner* — Richard Hutson
(74) *Attorney, Agent, or Firm* — David J. Aston; Peters Verny, LLP (57) ABSTRACT

Methods and compositions are provided for assaying for enzymes capable of releasing an enzyme donor fragment (ED) conjugated to a nucleic acid strand bonded to a surface. Conveniently, the beads are magnetic allowing segregation of the beads during the determination. Upon addition of enzyme acceptor fragment (EA) and substrate to the assay mixture, the method allows for discrimination between ED free in solution and ED bound to the bead. The complexing of ED and EA provides an active β-galactosidase enzyme. The method permits the assay of any substance involved in a pathway that can result in a reaction releasing the ED.

9 Claims, 2 Drawing Sheets

ASSAYS FOR NUCLEIC ACID MODIFYING ENZYMES

This application claims priority to Provisional Patent Application Ser. No. 60/305,047, filed Jul. 12, 2001.

BACKGROUND OF THE INVENTION

Field of the Invention

The field of this invention is the determination of nucleic acid modifying enzymes.

Cellular biochemistry and physiology is essential to medical treatment. As an indication of the status of the cell and the response of the cell to changes in its environment, one can look at the changes in the proteins of the cell and how individual proteins are up or down regulated. In many situations, one is interested in events in the nucleus, which events include DNA replication, RNA transcription, DNA repair, DNA unwinding, DNA nicking, DNA ligation, etc. For each of these events there are enzymes that are essential to the process, as well as ancillary enzymes and other proteins that may be required for carrying out the required operation. Enzymes of interest include nucleases, such as restriction enzymes, nickases, endo- and exonucleases, etc., primases, topoisomerases, helicases, and the like. Since these enzymes are involved in cellular proliferation and protein expression, they play a vital role in the health and function of the cell. In addition, there are enzymes that produce products that can be monitored for the product, such as polymerases, e.g. DNA and RNA polymerases, reverse transcriptases, transcription factors, protein binding assays, where the footprint protects against cleavage, and the like.

Assays have been developed that rely upon the complexing of two fragments of the β-galactosidase enzyme, which when complexed provide an active enzyme. The assays have relied upon a conjugate of the smaller fragment, referred to as the enzyme donor or ED, with a ligand of interest. By having a competition between the ligand in the assay medium and the ligand-ED conjugate for a ligand binding protein, the rate at which an active complex is formed is reduced. Therefore, in the presence of ligand, the rate of formation of the product of β-galactosidase can be monitored and related to the amount of ligand in the medium. U.S. Pat. Nos. 4,378,428; 4,708,929; 5,037,735; 5,106,950; 5,362,625; 5,464,747; 5,604,091; 5,643,734; and PCT application nos. WO96/19732 and WO98/06648 describe assays using complementation of enzyme fragments. The methods are predicated on greatly enhancing the molecular weight and bulk of the ligand-ED conjugate by the binding of the ligand binding protein to the conjugate, as well as blocking the binding of the ligand binding protein to the conjugate with ligand in the assay medium The use of the indicated assay protocol for detecting nucleic acid enzymes is very attractive. The assay provides for amplification, allows for an easy readout of the enzyme product and is relatively insensitive to the sample matrix. There is, therefore, interest in finding procedures that would allow the use of the indicated protocol for the detection of enzymes that interact with nucleic acids.

DESCRIPTION OF RELEVANT ART

U.S. Pat. Nos. 4,378,428; 4,708,929; 5,037,735; 5,106,950; 5,362,625; 5,464,747; 5,604,091; 5,643,734 and PCT application nos. WO96/19732; and WO98/06648 describe assays using complementation of enzyme fragments. Assays for different nucleic acid modifying enzymes include: U.S. Pat. Nos. 5,958,696 for a solid phase helicase assay; 5,554,502 (see also WO95/08623) for nuclease activity; PCT application nos. WO00/58439 for helicase activity; WO99/50460 for detection of mRNA; WO98/07869 for RNase H activity. Articles of interest include: Earnshaw and Pope, *J. Biomolecular Screening*, 6:39-46 (2001) describing flash scintillation proximity assays for characterization and screening of polymerase, primase and helicase activities; *BioTechniques*, 27:538-552 (1999) for high-throughput single nucleotide polymorphism genotyping by fluorescent 5' exonuclease assay; *Nucleic Acid Res.*, 23:3359-60 (1995) for high throughput RNase H protection assay; *Anal. Biochem.*, 222: 351-8 (1994) for colorimetric determination of DNase I activity with a DNA-methyl green substrate; *J. Immunol. Methods*, 155:249-56 (1992) for an antibody capture bioassay for DNase in human serum samples; *Nucleosides and Nucleotides*, 18:1277-78 (1999) for homogeneous reverse transcriptase and nuclease assays based on rare earth cryptate and fluorescent energy transfer.

SUMMARY

β-Galactosidase fragment (ED and EA) assays are employed for detection of nucleic acid modifying enzymes or compounds that affect nucleic acids. The enzyme donor (ED) is tethered to an inhibiting surface through a nucleic acid subject to enzyme modification, whereby upon such modification the ED is released from the inhibiting surface to bind to enzyme acceptor (EA) in solution in the presence of substrate. By monitoring the production of detectable product in the assay medium the activity of the nucleic acid modifying enzyme may be determined. The background resulting from binding of EA to bound ED conjugate does not interfere with the determination of the enzyme activity over a broad range of activities, while the nucleic acid modifying enzyme is able to interact with the nucleic acid tether to release the ED into solution.

DESCRIPTION OF THE SPECIFIC EMBODIMENTS

Protocols and reagents are provided for determining nucleic acid modifying enzyme activity, where the modification of the nucleic acid results in the release of a first β-galactosidase fragment into solution to become complexed with a second β-galactosidase fragment to form an active enzyme. The first β-galactosidase fragment is the enzyme donor, which is a small fragment of the enzyme. The ED is tethered to an inhibiting surface through a nucleic acid, which by itself or in conjunction with a hybridized nucleic acid serves as a substrate for a nucleic acid modifying enzyme. Release of the ED into an assay solution containing the enzyme acceptor results in an active β-galactosidase enzyme. By having substrate present in the assay solution and monitoring the formation of detectable product, one can relate the production of detectable product to the activity of the enzyme in solution.

In referring to "nucleic acid modifying enzymes" the key factor is that the enzyme is able to release the ED from the inhibiting surface. The manner in which this is achieved is not critical to this invention. While it will usually involve scission of a phosphate bond, it may be unwinding or other mechanism. The nucleic acid involved may be single or double stranded, DNA or RNA or other form of nucleic acid, e.g. protein nucleic acid, where the enzyme is able to cleave or unwind the strand.

The method has many applications in relation to nucleic acid modifying enzymes, as well as substances that can affect the ability of the nucleic acid modifying enzyme to modify the nucleic acid. Thus, the methodology may be used for a direct determination, where the interest lies in the nucleic acid modifying enzyme or a candidate compound affecting the enzyme activity, or where the interest lies in a different composition that provides for a result that affects the reaction of the nucleic acid modifying enzyme. The method may be used for determining the activity of a target enzyme, the presence of single nucleotide polymorphisms, the activity of enzyme inhibitors, the presence of a particular allele, where the alleles have different reaction rates, require different ancillary compounds or have different substrates and the like. Enzymes of interest include nucleases, both endo- and exonucleases, helicases, transposases, integrases, recombinases, topoisomerases, primases, or any other enzyme where the action of the enzyme will directly or indirectly result in the release of the ED from the inhibiting surface. The modification may be the result of unwinding of double stranded nucleic acid, cleavage, frequently as a result of a recognition sequence, mismatch, hybridization of RNA and DNA, nicking, or the like.

Indirect determinations may involve polymerases, transcription factors, DNA binding proteins, transposases, integrases, recombinases, and the like. All of these proteins are involved in the production or modification of nucleic acid, e.g. mRNA, spliceosomes, etc., so that the resulting mRNA may be captured and assayed using a different enzyme that results in release of ED from the inhibiting surface. The activity may be a result of the presence of an active enzyme, optionally for screening of compounds, where the activity is modulated by a candidate compound, activation of a proenzyme, the formation of a substrate with the ED oligonucleotide strand, e.g. formation of dsDNA with a restriction enzyme recognition sequence, formation of dsRNA, where the enzyme recognizes only the double stranded RNA, the presence of a transcription factor that initiates DNA strand formation that can then hybridize to the oligonucleotide bound to the ED to form a substrate for a nuclease, and the like.

The ED will be conjugated to the oligonucleotide in accordance with conventional procedures. The ED may be conjugated through a thioether, amide, ester, amino, or other convenient functionality as described in the literature and in the subject experimental section. Since the oligonucleotide must allow for release of the ED from the inhibiting surface, the oligonucleotide will usually be comprised of naturally occurring nucleotides, although where the enzyme can recognize unnatural nucleotides, these may also find application. Unnatural nucleotides include replacing oxygen with sulfur or nitrogen in the phosphate ester group, replacing the phosphate ester with an amino acid, changing the sugar from ribose to arabinose, and the like. These modifications may find advantage where the sample has enzymes that might interfere with the assay, e.g. degrading the oligonucleotide. Generally, the oligonucleotide will be of at least about 6, more usually at least about 8, preferably at least about 12 units, and not more than about 60, more usually not more than about 40 and preferably not more than about 30 units.

Where the conjugate is hybridized to a second strand, the second strand may be comprised of naturally occurring or synthetic nucleotides, depending upon the nature of the nucleic acid modifying enzyme. The length of the second strand is not limiting, so long as the ED conjugate bound to the surface does not form an undesirable level of active β-galactosidase complex. The second strand may be derived from naturally occurring or synthetic sources. The nucleic acid will usually be single stranded and may be derived from chromosomal fragments, synthesized oligonucleotides, cloned DNA, viral nucleic acid, plasmids, kinetoplast DNA, etc. The second strand may be bound directly to the inhibiting surface or may bound through hybridization to the ED conjugate. The second strand will usually be at least about 6 nucleotides, more usually at least about 10 nucleotides and may be of any greater length, as indicated above.

As indicated, the subject methodology may be used for determining enzyme activity in a sample, where the interest is in determining the amount of active enzyme present or where the interest is in determining the effect of a candidate compound on the enzyme activity. Alternatively, the interest may lie in the nature of a nucleic acid sequence. In each case, the nature of the nucleic acid composition may vary. Where one is interested in enzyme activity, the oligonucleotide of the ED-conjugate will be designed to act as a substrate for the enzyme with release of the ED. As indicated, the nucleic acid may be single stranded, double stranded, dsDNA, ssDNA, dsRNA, ssRNA, DNA-RNA duplex, or combinations thereof. In each case at least one strand will be bound, covalently or non-covalently to the inhibiting surface. Binding may be by forming a bond between the nucleic acid moiety and the surface, either directly or through a linker, the use of ligand-receptor binding, where the ligand may be the nucleic acid and the receptor may be a nucleic binding protein, such as a transcription factor, SSB protein, recA, polymerase protein components, antibody to nucleic acid or a particular sequence, a ligand bound to the nucleic acid and a receptor bound to the surface, etc., adsorption, nucleic acid hybridization, etc.

The linker between the oligonucleotide and ED may be varied as described in the literature for substances other than oligonucleotides. Conveniently, one may have a cysteine available in ED and modify a terminal or other nucleotide in the oligonucleotide to have a sulfur accepting functionality, such as an activated double bond, e.g. maleimido, an active halogen, e.g. α-halomethylcarbonyl, etc. For the most part, the linker will be relatively short, usually not more than about 10 atoms in the chain, more usually not more than about 6 atoms in the chain, where with a cyclic group, the smallest number of atoms will be counted.

For enzymes that directly interact with nucleic acid and can release the ED, different moieties may be used for their assay. For nucleases, one may use dsDNA that has a sequence recognized by the nuclease, where upon cleavage of the dsDNA, the ED is released from the inhibiting surface. For helicases and topoisomerases, one may use dsDNA, that will be unwound by the helicase or topoisomerase. For RNA-DNA hybrids, one may have the ED on either chain and depending upon the activity of the enzyme cleave or degrade the RNA or DNA chain. For degradation of the nucleic acid chain, enzymes such as *E. coli* RNase H1 (Crooke, et al. *Biochem. J.*, 312 (Pt. 2): 599-608 (1995) and DNA recombinase Flp (Xu, et al., *Mol. Cell*, 1:729-39 (1998) are exemplary.

Instead of measuring the effect of an enzyme on nucleic acid directly, one may provide for release of the ED indirectly, by acting on a product of the enzyme of interest. Such enzymes may include polymerases, primases, integrases, transposases, telomerases, recombinases, or other enzyme that provides for a product from which the ED may be released, where the product will usually be double-stranded nucleic acid capable of cleavage by a nuclease. In this instance, for example, using a polymerase, one would have the polymerase extend a chain resulting in a restriction enzyme recognition sequence. By adding the restriction enzyme to the assay medium, when the polymerase has extended the chain past the restriction recognition site, cleavage would occur with release of ED. Similarly, the primase can be used in conjunction with the polymerase to create the recognition site. For integrases and transposases, the integrated sequence would carry with it the restriction site. One would incubate the assay mixture in the absence of the restriction enzyme, terminate the integration reaction by denaturing the enzymes and then add the restriction enzyme. By measuring the β-galactosidase activity, one would have a measure of the activity of the other enzymes. Since the fragment being integrated will include the recognition sequence, it will normally be undesirable to have the restriction enzyme present during the integration stage.

Because one can measure the result of the activity of an enzyme of interest or a protein associated with a nucleic acid modifying activity, one can measure the activity of any component affecting the activity of such enzymes. Proteins that affect nucleic acid processes include transcription factors, kinases, proteases, phosphatases, acylases, synthetases, transferases, etc. By providing for a cascade or pathway where the ultimate step involves the ED-nucleic acid chain linked to the inhibiting surface, one can quantitatively or semi-quantitatively measure the activity of the protein of interest involved in the cascade. For example, if one is interested in a transcription factor that binds to a specific sequence of DNA and recruits the polymerase to the site, then by measuring the formation of the restriction enzyme recognition sequence through the release of the ED, one can then measure the activity of the transcription factor. Where one is interested in caspases, one can monitor the caspase and inhibitors thereof, by monitoring a DNase activated by one or more caspases. Where one is interested in mRNA, the single strand by which the ED is tethered to the inhibiting surface is selected to be complementary to the mRNA. An enzyme that can cleave duplex RNA in the presence of a gap is described by Wu et al., *J. Biol. Chem.*, 273:2532f-42. Of course, one may use reverse transcriptase to provide cDNA, followed by PCR, where the primer can have a restriction enzyme recognition site. By having the complementary sequence for linking the ED to the inhibiting surface, upon annealing, in the presence of the appropriate restriction enzyme, the ED would be released. Other protocols may be devised in light of the flexibility of the subject system and the availability of enzymes that cleave nucleic acid strands or unwind double stranded nucleic acid.

The inhibiting surface can be any solid or gel surface permits cleavage of the nucleic acid, while reducing the rate of production of the β-galactosidase product at the inhibiting surface. The surface may be particles, walls of a chamber, e.g. wells of microtiter well plates, films, slides, capillaries, chips, etc., porous or non-porous, or the like, preferably particles. The particles may be magnetic or non-magnetic, where the magnetic particles allow for ease of segregation. For particles, one may use latex particles, magnetic particles, agarose particles, etc. Particles may be used that are employed in nucleic acid synthesis, where the linking nucleic acid may be synthesized on the particles. The nucleic acid oligomer may be linked to the surface by any conventional linking group. The surface may be plastic, cellulosic, metal, silicon, or the like, being treated as appropriate to inhibit surface activity unrelated to the inhibition. So long as the surface does not interfere with the release of the ED, any surface may be used that is convenient for the assay.

The particles may be of a size in the range of about 0.1µ to 1 mm, usually about 5µ to 500µ. The beads should be dispersible in the medium and interference with the assay may be further reduced by segregating the beads from the supernatant, using a magnetic field with magnetic beads, and centrifugation, filtration, etc., with non-magnetic beads.

The linker to the surface is conveniently the linker employed with the synthesis of the oligonucleotide. Numerous linkers are reported in the literature. The solid-phase support will typically be comprised of small porous beads or particles in the form of a resin or gel. Numerous materials are suitable as solid-phase supports for the synthesis of polynucleotides. In general, such supports provide good mass transfer in and out of their pores, are chemically inert, minimally affected by reagents and solvents, and allow derivatization, attachment and removal of the oligonucleotide. Solid-phase materials include polystyrene derivatives, controlled pore glass, aluminum oxide beads, and silica beads. Conveniently, long chain alkyl amine control Pore Glass (LCAA-CPG) is available from Pierce Chemical, which may be derivatized by coupling deoxynucleoside 3'-O-succinic acid derivatives to the glass beads. Such nucleoside-derivatized LCAA-CPG is available from American Bionuclear, Emeryville, Calif. The size of the solid-phase beads may vary from about 5 to 500µ. The linker will usually have a chain of at least about 6 atoms, more usually at least about 10 atoms and not more than about 30 atoms, usually not more than about 20 atoms, where the atoms are carbon, oxygen, nitrogen, sulfur and phosphorous. See, for example, U.S. Pat. Nos. 4,517,338 and 5,449,767, as well as Mateucci, et al., *JACS*, (1981) 103:3185.

The general conditions for carrying out the assays using ED-EA complexing to form β-galactosidase are as follows. Where one is screening for active compounds, the target protein may be obtained from any source. The target proteins, usually enzymes, may be substantially pure, greater than about 90%, may be a mixture of enzymes of the same or different classification, may share the same coenzyme, may be a fraction from a naturally occurring source, e.g. cells, tissue, biological fluid, such as blood, saliva, urine, etc., biopsy, soil, water, etc. The sample may be a lysate, a lysate that has been fractionated, enriched for particular components, or the like. Enrichment may be achieved using chromatography, electrophoresis, density gradients, affinity columns, etc. The particular sample is not critical to this invention, since the reagents are robust and diverse components may be present without interference with the assay. Of course, components that change the binding affinity of the target enzyme(s) are to be avoided and will normally be removed prior to performing the assay. Where the enzyme is a member of a mixture of enzymes and the other enzymes have a similar reaction profile, one may wish to extract the enzyme of interest, for example, using affinity chromatography. Where one is interested in a compound having broad spectrum activity, active with at least two different enzymes, using a mixture of enzymes may be desirable. If a crude mixture is known to have a plurality of proteins that modify nucleic acids, the screen will indicate if a compound is active against one or more of the proteins and one can then determine which of protein that was.

The candidate compound may be naturally occurring or synthetic, may be extracted from a natural source, be a component of a mixture, a member or mixture of members of a combinatorial library, and the like. The compound will normally be an organic compound, including metalloorganic compounds, and may be aliphatic, aromatic, alicyclic, or heterocyclic or combination thereof, may be oligomeric, e.g. proteins, nucleic acids and polysaccharides, polar or non-polar, salts and neutral compounds, etc., and combinations thereof. Compounds of interest will generally have a molecular weight of at least 125 and may be 50 kDa or more, particularly where the compound is oligomeric. For small drugs, the drugs will have a molecular weight generally in the range of about 125 to 2000 Da, more usually not more than about 750 Da. The compounds will usually be composed of carbon, hydrogen, nitrogen, oxygen, sulfur, phosphorous, halogen, and may include metal atoms, particularly as ions.

The assay will normally be performed in an aqueous buffered medium selected for obtaining the desired binding and/or reactivity of the interacting components, e.g. candidate compound with target protein, nucleic acid strand duplexing with another strand, enzyme with nucleic acid, etc., where the medium may be changed at the different stages. For the determination of the release of the ED and complexing with EA, usually the pH of the medium will be in the range of about 3-11, more usually in the range of about 5-9. The volume of the assay composition is primarily one of convenience, taking into consideration the cost of the reagents, the available equipment, the number of assays to be performed, the sensitivity of detection, and the like. The assay may be performed in microtiter plate wells, ranging from 96 well plates to about 1536 well plates. The volumes may be from about 10 nl to 1 ml, usually varying from about 50 nl to 500 µl, preferably from about 10 to 250 µl. The concentration of the reagents, the ED-conjugate and the EA, will vary with the concentration range of the nucleic acid modifying enzyme and the protein influencing such enzyme. The concentrations of the components, ED-conjugate, EA and target protein may be determined empirically to optimize the sensitivity of the assay for the particular protein. Generally, the concentration of the ED-conjugate will be in the range of about 1-100, usually about 2-25 times the concentration of the test compound, and in those situations where the amount of test compound is unknown, times the average of the highest and lowest concentrations that can be estimated. The EA will be at least equal to the ED-conjugate and may be in substantial excess, usually not greater than about 10-fold excess. The equations for defining the concentrations are found in U.S. Pat. No. 4,378,428. The concentration of the nucleic acid modifying protein will be selected in accordance with the sensitivity of the assay and optimized for determining the activity of candidate compounds. Generally, one would wish to see a change of at least about 10% in the turnover of the substrate during the course of the assay, preferably at least about 15%. Generally, at least about 20% of the full dynamic range will be sufficient for the assay, preferably at least about 35% and more preferably at least about 50%. ("Full dynamic range" would be the range from the result in where all of the ED is released and where none of the ED is released.)

Concentrations of the compound of interest, enzyme, candidate compound, protein, nucleic acid, etc., may be as low as 1 pM and generally not more than about 0.1 mM, usually in the range of about 0.1 nM to 10 µM. Usually, there will only be one compound of interest in an assay, although mixtures may be used of up to about 10 different compounds, where rapid high throughput screening is desired and positive results deconvoluted.

The different components of the assay may be added simultaneously or consecutively. Usually, the compound of interest will be present before the ED-conjugate and EA are combined with the substrate. The order of addition will usually be adding the components of the upstream reaction and allowing incubation to occur for sufficient time to produce a product. At this time the reaction may be quenched and the medium added to the ED-reagent. Where the upstream component is a nucleic acid modifying protein which acts directly on the ED-reagent, then in screening, the candidate compound may be incubated with the modifying protein for sufficient time for complex formation followed by the addition of the ED-reagent and performance of the assay with the remaining agents. The incubation with the nucleic acid modifying protein and the ED-reagent will be varied in accordance with the nature of the nucleic acid modifying protein, its rate of reaction, the required sensitivity, and the like. Incubations will usually be carried out at a temperature in the range of about 15 to 50° C., more usually in the range of about 15 to 40° C., where the incubation may be temperature controlled. An appropriate buffer for the enzyme will be employed. After sufficient time, the other components may be added and the temperature maintained at the incubation temperature or a different temperature in the same range.

A single point after initiation of the reaction may be taken or a plurality of points at different times. Generally, the total reaction time will be for at least 5 min, usually at least 15 min and not more than about 10 h, usually not more than about 6 h, and more usually not more than about 3 h. The assay may be divided into two stages, a first incubation stage where the candidate compound reacts with the target enzyme or protein and a second product stage, where the remaining components of the assay are added and the turnover determined. The first stage will generally be at least 5 min, more usually at least 15 min and usually not more than about 6 h, usually not more than about 3 h. The second stage will usually be about 5 min, more usually at least about 15 min and generally not more than about 2 h, usually not more than about 1.5 h. The times for each of the stages will be selected to provide the necessary sensitivity for detection of the affinity for the target enzyme protein of the candidate compound.

During the incubation stage, the reaction can be allowed to occur while measurements of other samples may be performed. In this way, by appropriate staggering of the samples, the reader device can be in relatively constant use, so that times between measurements of different samples can be very short. Large numbers of assays with different samples may be performed in microtiter well plates, so that incubation occurs simultaneously, reagents can be added simultaneously and the reading can be performed simultaneously. In addition, one or more wells can be used as controls, so that one has an immediate direct comparison between the samples and the controls. The substrate turnover will usually be monitored spectrophotometrically, although it may be monitored electrochemically, etc., including absorption, fluorescence, chemiluminescence, etc.

The activity of the candidate compound as well as the activity of the nucleic acid modifying protein is measured as a direct function of the activity of the β-galactosidase enzyme. Enzyme activity is monitored by the appearance of a product of the enzymatically-catalyzed reaction or by disappearance of the enzyme substrate. This is the rate of conversion of substrate. Substrates for β-galactosidase that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbelliferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galacto-pyranoside, 5-bromo-4-chloro-3-indolyl-β-D-galactopyranoside, resorufin-β-D-galactopyranoside, 7-hydroxy-4-trifluoromethylcoumarin, u-nitrostyryl-β-D-galactopyranoside, and flourescein-β-D-galactopyranoside.

One or more controls can be employed, where the controls may lack a candidate compound, have a known amount of a compound of known activity or a plurality of known amounts or known compounds, so as to have an affinity ratio for the candidate compound as related to known compounds. By graphing the results with known amounts of compounds having known affinities, one can compare the results with the candidate compound. Where mixtures of target proteins are involved, one can relate the average activity to the affinity of the compound. One may then deconvolute as to the individual target proteins. For the nucleic acid modifying enzyme, controls may be using a known amount of the enzyme, the absence of the nucleic acid modifying enzyme or using a different method for releasing ED.

In preparing the ED-conjugate, the oligonucleotide will be selected in accordance with the target enzyme protein. The oligomer may be synthesized using an automatic apparatus on a solid support in accordance with conventional procedures. The ED may then be coupled to the oligomer. Conveniently, cysteine can be provided as a member of the ED and the oligomer may be modified with a mercapto-reactive functionality, e.g. active halogen, activated olefin, etc. These chemistries are amply described in the literature. See U.S. Pat. No. 5,643,734 for specifics of ED-conjugate and EA preparations, which disclosure is specifically incorporated herein.

More particularly, carrying out the assay, the sample is combined with the tethered ED. Where one is interested in enzyme activity with the nucleic acid tether, the conditions will be selected to substantially optimize the enzyme activity. The assay where the interest is in the enzyme activity, intrinsic to the sample or as modified by a candidate compound, the nucleic acid linking the ED to the inhibiting surface will be a substrate for the enzyme and the reagent and the sample will be combined under conditions where the enzyme is active. Each enzyme will usually have a preferred buffer with various constituents, such as trace metals, ancillary compounds, etc., and at a preferred pH and temperature. The EA may be added in a separate step in conjunction with the substrate or the substrate added afterwards, after the ED and EA have had time to complex. Where the interest is in the nucleic acid in the sample, the sample will be combined under conditions where the nucleic acid of interest anneals to the nucleic acid ED linker. The resulting duplex may then be washed free of the medium and other components of the sample. This will be followed by the addition of the other reagents including the nucleic acid modifying enzyme and the EA may be included or added subsequently. The substrate for the β-galactosidase may be added with the EA or subsequently.

Specifically, for assaying for nucleases, a nucleic acid reagent is prepared where one strand is covalently linked to an inhibiting surface, conveniently beads. The second strand is then added, optionally in substantial excess, e.g. 2×, and allowed to anneal. Alternatively, one strand may be bonded to a ligand, and annealed to the second strand. The duplex is then added to the inhibiting surface comprising the receptor. For example, biotin may be the ligand and strept/avidin may be bound to the surface. There are numerous examples of using biotin modified nucleotides in the literature to have biotin labeled oligonucleotides. The conditions for the annealing and ligand-receptor binding are conventional and do not need to be described here. The product may then be washed to removed any non-specifically bound nucleic acid. One of the strands will be bound to the ED, where in most cases the election of which strand will be conjugated to the ED will be a matter of convenience, particularly synthetic convenience. Once the ED-reagent (ED-linked to an inhibiting surface through an oligonucleotide linker) is prepared, it may then be combined with the sample.

The ED-reagent and the sample are combined under conditions where the nuclease is active and the mixture incubated. Usually the temperature for the incubation will be at or above room temperature, generally in the range of about 25-40° C. During the incubation, the mixture may be subjected to mild agitation. The time for the incubation will depend upon the reactivity of the nuclease, the anticipated concentration of the nuclease, the sensitivity of detection, and the like. Additional buffer may be added for the determination and optionally an aliquot of the medium transferred to another container.

The inhibiting surface may then be segregated from the supernatant by any convenient means, magnetic field, centrifugation, decanting, etc. Where the inhibiting surface is a particle, the particles may be segregated from the liquid medium and additional unmodified particles added, usually at least about 0.5-5× the number of particles in the container. The additional particles serve to further reduce the background.

Convenient containers are microtiter well plates that have well-established readers for detecting the signal produced by the β-galactosidase product. To the medium may then be added the EA, generally in a ratio of about 10-10$^5$, usually 10-10$^4$, to the ED present in the assay medium based on the prior dilution(s) and transfer. The substrate may be conveniently added concurrently or subsequently. After sufficient time to obtain a signal from the product of the substrate, usually requiring at least about 1 min, more usually at least about 5 min and not more than about 120 min, usually about 15 to 90 min, a single reading may be taken or a plurality of readings may be taken during the reaction period and the rate of reaction determined. One or more standards may be used, such as a sample having a known amount of enzyme, a sample without enzyme, etc. Where candidate compounds are being investigated, one or more samples may be prepared with different concentrations of the candidate compound and again comparisons may be made with controls, where an additional control would be the sample without the candidate compound and/or with a compound of known activity.

For other enzymes, similar protocols would be employed, where the variation would be in the oligonucleotide linker and the conditions associated with the particular enzyme.

Where one is interested in a particular sequence, then the sample would be processed to make the sequence, if present, available for annealing to the oligonucleotide linker. Thus, for cells where one is interested in mRNA, one would prepare a lysate, isolate the mRNA and then add the mRNA to the ED-reagent under annealing conditions. Using an enzyme that cleaves the oligonucleotide only when duplexed, the presence of the target mRNA would result in the release of the ED. Alternatively, one could use PCR with a primer having a restriction enzyme recognition sequence, where the oligonucleotide has the complementary sequence to the primer and a portion of the cDNA. Under the appropriate annealing conditions, only extended primer would bind, so that the presence of cDNA would result in cleavage and release of the ED. For detecting single nucleotide polymorphisms, the oligonucleotide linker would differ from the target sequence at the allelic site, so that when the allele is present, there would be a mismatch. By using a nuclease that removes the mismatched nucleotide and having annealing conditions that results in the melting of the truncated sequence, the ED would be released. By having only a few nucleotides duplexed between the ED and the mismatch, generally from about 3-12, the ED bound oligonucleotide would be rapidly melted and the ED released.

The various protocols indicated above can be used as the readout for many proteins that are involved with replication, transcription, extension, etc., by devising ED-reagent that will interact with the product to give a readout that can be related to the protein of interest or a compound that modulates the activity of the protein of interest.

For convenience, kits can be provided comprising the ED-reagent, EA, substrate and controls, as appropriate for the purpose of the assay. Particularly, the ED-reagent can be provided conjugated to beads.

The following examples are offered by way of illustration and not by way of limitation.

EXPERIMENTAL

The following is a general protocol for nuclease assays:
Combine 5 µl of Reagent I or II, 2 µl of nuclease and 18 µl of assay buffer. Incubate at 37° C. for 30 min on a shaker. Add 80 µl of ED dilution buffer and 20 µl/well of DNase assay buffer and allow to stand for one minute above a magnet. Add 10 µl of EA and 10 µl of β-galactosidase substrate and incubate for 60 min. Read fluorescence in each well as RLU.

Example 1

Preparation of 1,2-bismaleimidoethane-Enzyme Donor (4) (BMOE-ED4) Conjugate

To a solution of the ED4 (amino acid sequence=H$_2$N-MDPSGNPYGIDPTNSSPGNID-PRASSNSLAVVLNRRDWENPGVTNLNRLAAHPPFA SWRNSEEARTDCPSNNLANPEWGLESRSAGMPLE-CO$_2$H (SEQ. ID NO: 1), 10 mg, 1.01 µmole) in 0.75 mL of HPLC buffer C (0.1% trifluoroacetic acid in HPLC water) was added a solution of 1,2-bismaleimidoethane (1.4 mg, 6.49 µmole) in DMF (0.75 ml). The solutions were well mixed by vortexing, where the mercapto moiety of the cysteine at position 67 from the N-terminus of the ED4 reacts with only one of the maleimide groups of BMOE to produce BMOE-ED4. To this was added sodium phosphate buffer (100 mM, pH=8.0, 0.5 mL). The pH of the solution was measured to be in 7.0-8.0 range. Allowed the reaction to proceed for 10 min. Increased the volume to 2.5 mL by adding HPLC buffer C (0.5 mL) to the reaction mixture. Exchanged the buffer on a Sephadex G-25 column (PD-10 from Pharmacia) pre-equilibrated with HPLC buffer C. Purified the conjugate by HPLC using a step gradient of 20 to 40 percent HPLC buffer D (0.1% TFA in HPLC grade acetonitrile) at 4 mL per minute. The column used in this purification was a silica gel C4 reversed phase column (5-micrometer particle size, 1×25 cm dimension). The purification was monitored using a UV detector at 260 nm. The product eluted at 18.7 minutes. This yielded pure ED4-BMOE (7.23 mg, 71% of the theoretical yield) as quantitated by UV absorbance of the solution at 280 nm ($\epsilon_{280}$=16,500 cm$^{-1}$M$^{-1}$). The product was confirmed by ESI-MS (10064=M+1).

Example 2

Deprotection of the [A]$_{20}$-C$_3$—S—S—C$_3$—OH Oligonucleotide

Dissolved oligonucleotide [A]$_{20}$-C$_3$—S—S—C$_3$—OH (Sequence=AAAAAAAAAAAAAAAAAAAA-C$_3$H$_6$—S—S—C$_3$—OH (SEQ. ID NO:2), thiol functionalized at the 3' end, 1 mg, 154 nanomoles) in 0.5 mL of HPLC grade water. Prepared a fresh solution of DTT (0.5 M) in sodium phosphate buffer (100 mM, pH=8.4). A solution of DTT (40 µL) was added to the oligonucleotide solution (150 µL, ~0.59 mg, 91 nanomoles). Let the reaction stand for 60 min. Purified the conjugate by HPLC using a step gradient of 0 to 20% HPLC buffer B (HPLC grade acetonitrile) at 4 mL per minute. HPLC buffer A (20 mM triethylammonium acetate, pH 6.5) was used for the balance of the gradient. The column used in this purification was a reversed phase C4 silica gel column (5-micrometer particle size, 1×25 cm dimension). The purification was monitored using a UV detector at 260 nm. The product eluted at 18.2 minutes. This product ([A]$_{20}$-SH) was used for the preparation of the conjugates without further characterization.

Example 3

Preparation of [A]$_{20}$-BMOE-ED4

A solution of [A]$_{20}$-SH (0.8 mL, 0.236, 36 nanomole) was added to a solution of BMOE-ED4 (200 µL, 0.25 mg, 25 nanomole). To this was added sodium chloride (9.6 mg), sodium phosphate buffer (100 mM, pH=8.4, 0.2 mL) and dimethyl formamide (DMF, 0.2 mL). Let the reaction stand for 10 minutes. Purified the conjugate by HPLC using a step gradient of 20 to 40% HPLC buffer B (HPLC grade acetonitrile) at 4 mL per minute. HPLC buffer A (20 mM triethylammonium acetate, pH 6.5) was used for the balance of the gradient. The column used in this purification was a silica gel C4 reversed phase column (5-micrometer particle size, 1×25 cm dimension).

The purification was monitored using a UV detector at 260 nm. The product eluted at 9.9 minutes. The peak was characterized by absorbance at 260 nm (A$_{260}$) due to the dominance of the oligonucleotide absorbance ($\epsilon_{260}$=304000 cm$^{-1}$M$^{-1}$). This peak complemented with enzyme acceptor, and showed beta-galactosidase activity. HPLC analysis demonstrated a single peak for the conjugate.

Example 4

Preparation of Rb1-4-BMOE-ED4

To a solution of Rb1-4-NH2 (Sequence=CTTTGGCCACG (SEQ. ID NO:3) (iAmMC6T) GCGCATTC (SEQ. ID NO:4), where iAmMC6T is 5-(4,11-diaza-1-en-3-oxoundecane)-2'-deoxyuridine; a deoxythymidine analog containing a primary amino group, 0.2 mg in 50 µL of HPLC grade water, 32 nanomoles) was added 1.5 mL of sodium phosphate buffer (100 mM, pH=8.0). To this was added 2-iminothiolane hydrochloride (2-IT, 1.8 mg). The mixture was vortexed for complete dissolution. Let the reaction mixture stand for 30 min. At this point the pH of the solution was around 7.4. At this point, to the reaction mixture was added dithiothreitol (7.4 mg). Let the mixture stand for 30 min. Increased the volume to 2.5 mL and desalted the mixture on a Sephadex G-25 column (PD-10 column from Amersham-Pharmacia) pre-equilibrated with HPLC buffer A (20 mM triethylammonium. {TEA} acetate in HPLC water pH=6.5). Purified the oligonucleotide by HPLC using a step gradient of 20 to 40% HPLC buffer B (HPLC grade acetonitrile) at 4 mL per minute. HPLC buffer A (20 mM TEA acetate, pH 6.5) was used for the balance of the gradient. The column used in this purification was a silica gel C4 reversed phase column (5-micrometer particle size, 1×25 cm dimension). The purification was monitored using a UV detector at 260 nm. The thiolated oligonucleotide elutes at 14.6 min. To this entire fraction containing the thiolated oligonucleotide (~2 mL) was added BMOE-ED4 (40 µl, 20 µg, 2 nanomoles). Added sodium phosphate buffer (100 mM, pH=8.4, 0.1 mL) to adjust the pH to 6.0 to 7.0. The reaction mixture was vortexed, and let stand for 30 min. The reaction volume was increased to 2.5 mL by adding HPLC buffer A. This was subsequently desalted on a Sephadex G-25 column (PD-10 from Amersham-Pharmacia) pre-equilibrated with HPLC buffer A. The conjugate was purified by HPLC using a gradient of 0 to 50% HPLC buffer B (HPLC grade acetonitrile) in 50 minutes at 4 mL per minute. HPLC buffer A (20 mM TEA acetate, pH 6.5) was used for the balance of the gradient. The column used in this purification was a reversed phase silica gel C4 column (5-micrometer particle size, 1×25 cm dimension). The purification was monitored using a UV detector at 260 nm. The conjugate eluted at 31.7 min under these conditions. The conjugate was quantitated (3.9 µg, 0.24 nanomoles) using absorbance at 260 nm ($\epsilon_{260=221600}$ cm$^{-1}$M$^{-1}$). HPLC analysis showed the conjugate as a single peak with maximum absorbance at 260 nm.

Example 5

Deprotection of the H22-C$_6$—S—S—R Oligonucleotide

Dissolved oligonucleotide H22-C$_6$—S—S—R (GTTTTCCCAGTCACGACGGTTGT-O—C$_6$H$_{12}$—S—S—R (SEQ. ID NO:5) with thiol functionalization at the 3' end, 40 µg, 6 nanomoless) in 0.5 mL of HPLC grade water. To the reaction mixture was added dithiothreitol (5 mg). The reaction mixture was vortexed well and let stand for 90 min. At this point the reaction mixture was passed through a Sephadex G-25 column (NAP-5 from Amersham-Pharmacia) pre-equilibrated with sodium phosphate buffer (100 mM, pH 6.5 with 2 mM ethylenediaminetetraacetic acid). This oligonucleotide solution (0.25 mL) was purified by HPLC using a step gradient of 0 to 20% HPLC buffer B (HPLC grade acetonitrile) at 4 mL per minute. HPLC buffer A (20 mM TEA acetate, pH 6.5) was used for the balance of the gradient. The column used in this purification was a silica gel C4 reversed phase column (5-micrometer particle size, 1×25 cm dimension). The purification was monitored using a UV detector at 260 nm. The product eluted at 14.7 minutes. This product (H22-SH) was used for the preparation of the conjugates without further characterization.

Example 6

Preparation of H22-BMOE-ED4

To a solution of BMOE-ED4 (100 mL, 50 mg, 5 nanomoles) was added a solution of H22-SH (~2 mL, ~10 mg, ~1 nanomoles). To this was added sodium phosphate buffer (100 mM, pH=7.0, 0.2 mL). Let the reaction stand for 90 minutes.

Purified the conjugate by HPLC using a step gradient of 20 to 40% HPLC buffer B (HPLC grade acetonitrile) at 4 mL per minute. HPLC buffer A (20 mM TEA acetate, pH 6.5) was used for the balance of the gradient. The column used in this purification was a reversed phase C4 silica gel column (5-micrometer particle size, 1×25 cm dimension). The purification was monitored using a UV detector at 260 nm. The product eluted at 9.4 minutes. The peak was characterized by absorbance at 260 nm (A260) due to the dominance of the oligonucleotide absorbance (e260=246700 cm$^{-1}$M$^{-1}$). This peak complemented with enzyme acceptor, and showed β-galactosidase activity. HPLC analysis demonstrated a single peak for the conjugate.

DNaseI cleaves oligonucleotide from ED/oligo-biotin/magnetic beads complex to form active enzyme providing amplification signal.

Methods: PolyT25 magnetic beads (Dynal) were hybridized with ED4A20 (300 µl, 1 nM) at room temperature for 1 h on shaker. The beads were washed 4× with EDDB (ED dilution buffer; 10 mM MES, 200 mM NaCl, 10 mM EGTA, 2 mg/ml BSA fragment, 14.6 mM NaN3, pH 5.5)) to remove free ED, if any. Divide the beads into 3 tubes, remove the supernatant, add DNaseI (2 µl, 0.5 µl or 0; 7.5 unit/µl, Amersham) and 20 ml DNase assay buffer (40 mM Tris, 6 mM MgCl$_2$). After incubating at 37° C. for 10 min add 80 µl EDDB to bring the volume up to 100 µl. Transfer 20 µl/well (10 fmole ED-oligo/well) to 384-well plate on a magnet for 1 min, add 5 µl/well plain beads, then add 20 µl of EA/substrate (0.1×EA, 80 ug/ml resorufin) to each well.

Incubate 1 h, then read by FluoroCount (Packard serial #424090) using 530/610 nm for excitation and emission, PMT (volts) 700, Gain level: 1, read length 0.2 sec. 4 replicates for each treatment.

TABLE 1

| ED4-A20 | 10 fmole/well | | |
|---|---|---|---|
| DNaseI nM | 80 | 20 | 0 |
| net | 1717 | 657 | 45 |
| ratio | 38 | 15 | 1 |

Results as seen in Table 1, DNaseI cleavage provides active ED to form beta-galactosidase complementation. DNaseI cleavage gives a ratio of 38 and 15 compared to the one without DNaseI.

Example 7

Two pmole of ED-oligo (ED4A20 or ED4Rb1-4) was hybridized to a large excess of its complementary sequence probe (70 pmoles of T$_{25}$Bt [Bt intends biotin] for ED4A20; Bt3C for EDRb1-4). The mixture was incubated 2 h at RT for EDA20/T25 and at 50° C. for ED4Rb1-4/Bt3C in a total volume of 100 µl 0.5×SSC. The duplexes were coupled to strepavidin-coated magnetic beads (Bang's Laboratory, Inc.) by incubating at RT for 20 min. The beads were washed 4× to remove any non-specifically bound or unstable ED. The beads were resuspended in 100 µl 0.5×SSC, 20 µl ED-oligo/µl. To 5 µl of beads was added DNaseI (3 µl or 0; 7.5 unit/ul, Amersham) and 20 µl DNase assay buffer (40 mM Tris, 6 mM MgCl$_2$). After incubating at 37° C. for 30 min on the shaker, 80 µl EDDB was added and transfer 20 µl/well (20 fmole ED-oligo/well) was added to individual wells of a 384-microtiter well plate and held over a magnet for 1 min. Unmodified beads (5 µl/well) were added, followed by adding 20 µl of EA/substrate (10 µl of 40 nM EA), 80 ug/ml resorufin galactoside) to each well. After incubating for 1 h, each well was read by FluoroCount (Packard serial #424090) using 530/610 nm for excitation and emission, PMT (volts) 700, Gain level: 1, read length 0.2 sec. Four replicates were employed for each treatment. The following Table 2 indicates the results.

TABLE 2

|  | ED4A20 |  | ED4Rbl-4 |  |
|---|---|---|---|---|
| Dnase I | 120 nM | 0 | 120 nM | 0 |
| net RFU | 2385 | 209 | 2083 | 433 |
| ratio | 11 | 1 | 5 | 1 |

Example 8

Three pmole of ED-oligo (EDH22) was hybridized to a large excess of its complementary sequence probe (100 pmoles of H60Bt; Biotin-c18 linker-5'GGTTTAAAAA ATAGGAGGGA CAACGTCGTG ACTGGGAAAA CTC-CCCGGGT ACCGAGCTCG-3') (SEQ. ID NO:6). The oligonucleic acids were heated at 95° C. for 5 min, then incubated at 50° C. for 1 h total in 100 µl 0.5×SSC. The hybrid was bound to strepavidin-coated magnetic beads (Bang's Laboratory, Inc.) by incubating at RT for 20 min. The beads were washed 4× to remove non-specifically bound ED. The beads were resuspended in 100 µl 0.5×SSC, 20 µl ED-oligo/µl. Five µl beads of the bead suspension was transferred to a well and DNaseI (7.5 unit/µl, Amersham) added in 20 µl DNase assay buffer (40 mM Tris, 6 mM MgCl$_2$). After incubating at 37° C. for 30 min on the shaker, 80 µl EDDB was added and 20 µl/well (20 fmole ED-oligo/well) transferred to a 384-microtiter well plate and held over a magnet for 1 min. To the solution was added 5 µl/well of plain beads, followed by the addition of 20 µl of EA/substrate (10 µl of 40 nM EA, 80 µg/ml resorufin galactoside) to each well. The assay medium was incubated for 1 h, then read by FluoroCount (Packard serial #424090) using 530/610 nm for excitation and emission, PMT (volts) 700, Gain level: 1, read length 0.2 sec. Four replicates were employed for each treatment.

Figure 1:
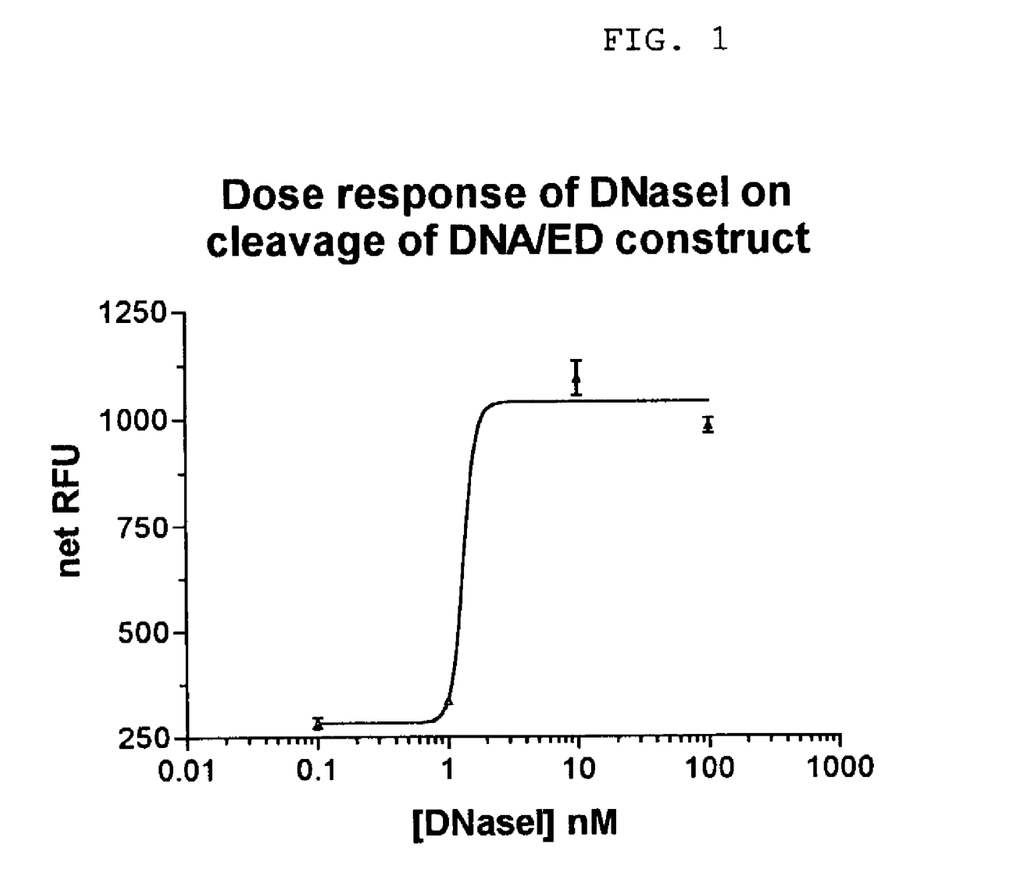
FIG. 1 is a graph representing a dose response of DnaseI on cleavage of DNA/ED Construct.
Figure 2:
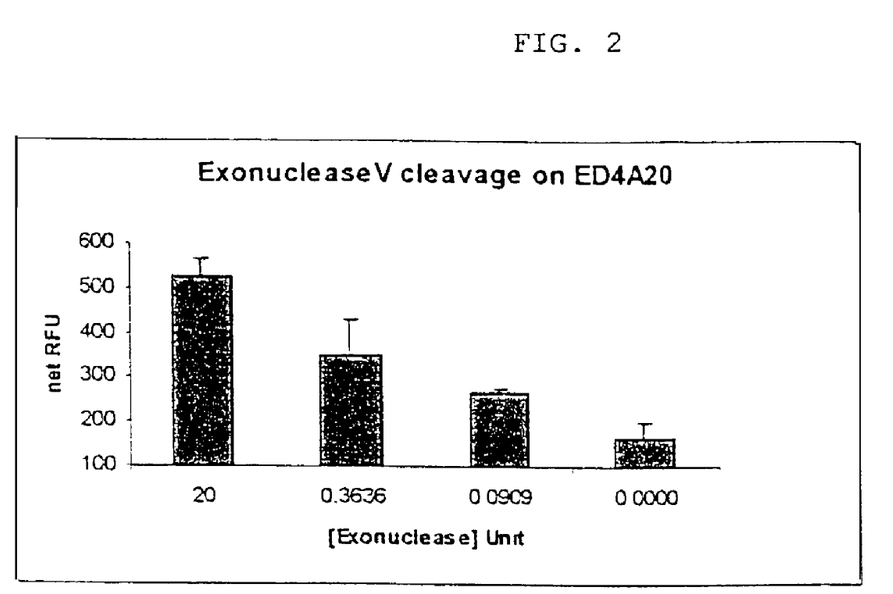
FIG. 2 is a graph representing exonuclease V cleavage on ED4A20.

Results are shown in FIG. 1. FIG. 1 shows that DNaseI cleavage provides active ED to form β-galactosidase complementation at dose dependence of nuclease. These data show the assay sensitivity is 0.8 nM of DNaseI giving a ratio of 2 compared to treatment without DNaseI. ED50 is 1.3 nM.

Example 9

PolyT25 magnetic beads (Dynal) were hybridized with ED4A20 (400 µl, 1 nM) at room temperature for 1 h on a shaker. The beads were washed 4× with EDDB (ED dilution buffer) to remove non-specifically bound ED. The beads were divided into 4 tubes, the supernatant removed, and ExonucleaseV (2 µl, 0.2 µl or 0.02 µl; 10 unit/µl Amersham) added with 20 µl ExonucleaseV assay buffer (66.7 mM glycine-NaOH buffer, pH 9.4, 30 mM MgCl$_2$, 8.3 mM 2-mercaptoethanol, 0.5 mM ATP). After incubating at 37° C. for 30 min, 80 µl EDDB was added to make a volume of 100 il. The solution (20 ul/well; 10 fmole ED-oligo/well) was transferred to 384-microtiter well plate and held over a magnet for 1 min, followed by the addition of 20 µl of EA/substrate (10 µl of 40 nM EA, 10 µl of 80 µg/ml resorufin galactoside) to each well. After incubating for 1 h, the results were read by FluoroCount (Packard serial #424090) using 530/610 nm for excitation and emission, PMT (volts) 700, Gain level: 1, read length 0.2 sec. Four replicates were performed for each treatment.

As shown below, ExonucleaseV cleavage provides active ED to form beta-galactosidase complementation. ExonucleaseV cleavage gives a ratio of 3 compared to the assay without ExonucleaseV.

TABLE 3

| ED4A20 | 10 fmole/well | | | |
|---|---|---|---|---|
| ExoV | 20 | 0.3636 | 0.0909 | 0.0000 |
| net | 526 | 351 | 265 | 166 |
| ratio | 3.2 | 2.1 | 1.6 | 1.0 |

It is evident from the above results that the subject methodology provides a robust method for determining the presence of enzymes that directly or indirectly result in the release of ED from a ED-conjugate. The methodology allows for determining a large number of different proteins that can be related to a nucleic acid assay through a pathway that results in the release of the ED and well as screening for the effect of candidate compounds on the role the target protein plays in such pathway. This can be illustrated by transcription factors, proteases that activate nucleases, and the like. In addition, one can monitor the presence of nucleic acid sequences, where hybridization of the nucleic acid sequence to the ED-reagent results in the release of the ED.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A method for detecting the effect of a test compound being tested for effect on nuclease activity, said method comprising:
   incubating in an assay medium said test compound, a nuclease which is either an endonuclease or exonuclease V, and an enzyme donor fragment (ED)-reagent for sufficient time for reaction of said ED-reagent and said nuclease, said ED-reagent comprising ED linked through an oligonucleotide strand of not more than 60 nucleotides to a magnetic bead,
   said reaction resulting in separating said ED from said magnetic bead;
   adding enzyme acceptor (EA) and a β-galactosidase substrate that allows for determination of an amount of turnover of said substrate;
   wherein said ED and EA are fragments of β-galactosidase, and said separating of said ED from said magnetic bead results in complexing of said ED and said EA to form an active β-galactosidase enzyme, and said ED reagent has substantially reduced ability to complex with said EA as compared to ED separated from said bead, thereby resulting in reduced background; and
   determining the amount of turnover of active β-galactosidase enzyme formed from said ED and said EA as a measure of the effect of said test compound on said nuclease activity.

2. The method according to claim 1, wherein said test compound is derived from at least one of a source of mRNA, a source of DNA, or a source of a nuclease activating enzyme, wherein said turnover is related to said mRNA, said DNA or said nuclease activating enzyme, respectively.

3. The method according to claim 2 wherein said source of DNA provides DNA complementary to said oligonucleotide strand.

4. The method according to claim 1, wherein unmodified beads are included in said assay medium prior to said determining.

5. The method according to claim 1, wherein said ED is bonded to a single stranded oligonucleotide strand bonded to said bead.

6. The method according to claim 1, wherein said ED is bonded to a second oligonucleotide strand hybridized to a first oligonucleotide strand bonded to said bead, whereby said ED is linked through an oligonucleotide strand to said magnetic bead.

7. The method according to claim 1, wherein prior to said adding, said magnetic bead is segregated by means of a magnetic field.

8. The method of claim 6 wherein said second oligonucleotide strand comprises synthetic nucleotides.

9. The method according to claim 1 wherein said endonuclease is a restriction enzyme.

* * * * *

SEQUENCE LISTING

```
<160> NUMBER OF SEQ ID NOS: 6

<210> SEQ ID NO 1
<211> LENGTH: 90
<212> TYPE: PRT
<213> ORGANISM: Artificial Sequence
<220> FEATURE:
<223> OTHER INFORMATION: synthetic construct ED4

<400> SEQUENCE: 1

Met Asp Pro Ser Gly Asn Pro Tyr Gly Ile Asp Pro Thr Asn Ser Ser
1               5                   10                  15

Pro Gly Asn Ile Asp Pro Arg Ala Ser Ser Asn Ser Leu Ala Val Val
            20                  25                  30
```

```
Leu Asn Arg Arg Asp Trp Glu Asn Pro Gly Val Thr Asn Leu Asn Arg
         35                  40                  45

Leu Ala Ala His Pro Pro Phe Ala Ser Trp Arg Asn Ser Glu Glu Ala
 50                  55                  60

Arg Thr Asp Cys Pro Ser Asn Asn Leu Ala Asn Pro Glu Trp Gly Leu
 65                  70                  75                  80

Glu Ser Arg Ser Ala Gly Met Pro Leu Glu
                 85                  90

<210> SEQ ID NO 2
<211> LENGTH: 20
<212> TYPE: DNA
<213> ORGANISM: Artificial Sequence
<220> FEATURE:
<223> OTHER INFORMATION: synthetic construct [A]20-C3-S-S-C3-OH
      Oligonucleotide

<400> SEQUENCE: 2
aaaaaaaaaa aaaaaaaaaa                                        20

<210> SEQ ID NO 3
<211> LENGTH: 11
<212> TYPE: DNA
<213> ORGANISM: Artificial Sequence
<220> FEATURE:
<223> OTHER INFORMATION: synthetic construct Rb1-4-NH2

<400> SEQUENCE: 3
ctttggccac g                                                 11

<210> SEQ ID NO 4
<211> LENGTH: 8
<212> TYPE: DNA
<213> ORGANISM: Artificial Sequence
<220> FEATURE:
<223> OTHER INFORMATION: synthetic oligonucleotide construct

<400> SEQUENCE: 4 gcgcattc                                                      8

<210> SEQ ID NO 5
<211> LENGTH: 23
<212> TYPE: DNA
<213> ORGANISM: Artificial Sequence
<220> FEATURE:
<223> OTHER INFORMATION: synthetic construct H22-C6-S-S-R
      Oligonucleotide

<400> SEQUENCE: 5
gttttcccag tcacgacggt tgt                                    23

<210> SEQ ID NO 6
<211> LENGTH: 60
<212> TYPE: DNA
<213> ORGANISM: Artificial Sequence
<220> FEATURE:
<223> OTHER INFORMATION: synthetic construct H60Bt

<400> SEQUENCE: 6
ggtttaaaaa ataggaggga caacgtcgtg actgggaaaa ctccccgggt accgagctcg   60
```